United States Patent

Moses et al.

[11] Patent Number: 5,837,680
[45] Date of Patent: Nov. 17, 1998

[54] PHARMACEUTICAL COMPOSITIONS COMPRISING TROPONIN SUBUNITS, FRAGMENTS AND ANALOGS THEREOF AND METHODS OF THEIR USE TO INHIBIT ANGIOGENESIS

[75] Inventors: Marsha A. Moses, Brookline; Robert S. Langer, Newton; Dimitri G. Wiederschain, Brookline; Inmin Wu, Boston; Arthur Sytkowski, Arlington, all of Mass.

[73] Assignee: Children's Medical Center Corporation, Boston, Mass.

[21] Appl. No.: 602,941

[22] Filed: Feb. 16, 1996

[51] Int. Cl.⁶ .................. C07K 14/47; C07K 14/435; A61K 38/00; A61K 38/04
[52] U.S. Cl. .................. 514/12; 514/21; 530/324
[58] Field of Search .................. 514/12; 530/324, 530/350

[56] References Cited

U.S. PATENT DOCUMENTS 5,583,200  12/1996  Larue et al. .................. 530/355

OTHER PUBLICATIONS

Auerbach et al., 1985, "Expression of organ-specific antigens on capillary endothelial cells", Microvasc Res 29:401–411.

Blood et al., 1990, "Tumor interactions with the vasculature: Angiogenesis and tumor metastasis", Biochem Biophys Acta 1032:89–118.

Boyden et al., 1962, "The chemotactic effect of mixtures of antibody and antigen on polymorphonuclear leucocytes", J Exp Med 115:453–466.

Brekke and Greaser, 1976, "Separation and characterization of the troponin components from bovine cardiac muscle", J Biol Chem 251:866–871.

D'Amore, 1986, "Growth factors, angiogenesis and metastasis", Prog Clin Biol Res 221:269–283.

Ebashi et al., 1968, "Troponin: Preparation and physiological function", J Biochem 64:465.

Falk et al., 1980, "A 48-well micro chemotaxis assembly for rapid and accurate measurement of leukocyte migration", J Immunol Methods 33:239–247.

Folkman, 1995, "Clinical applications of research on angiogenesis", New Eng J Med 333:1757–1763.

Folkman et al., 1983, "Angiogenesis inhibition and tumor regression caused by heparin or a heparin fragment in the presence of cortisone", Science 221:719–725.

Folkman, 1985, "Tumor angiogenesis", in *Advances in Cancer Research*, Klein and Weinhouse (eds.), Academic Press, NY, pp. 175–203.

Gahlmann and Kedes, 1990, "Cloning, structural analysis, and expression of the human fast twitch skeletal muscle troponin C gene", J Biol Chem 265:12520–12528.

Gartner et al., 1978, "Neovascularization of the iris (Rubeosis Iridis)", Surv Ophthamol 22:291–312.

Glaser et al., 1980, "Adult tissues contain chemo-attractants for vascular endothelial cells", Nature 288:483–484.

Hartshorne et al., 1968, "Fractionation of troponin into two distinct proteins", Biochem Biophys Res Comm 31:647–653.

(List continued on next page.)

*Primary Examiner*—Cecilia J. Tsang
*Assistant Examiner*—Michael Borin
*Attorney, Agent, or Firm*—Pennie & Edmonds, LLP

[57] ABSTRACT

The present invention relates to pharmaceutical compositions containing troponin subunits C, I, or T, or fragments thereof, in therapeutically effective amounts that are capable of inhibiting endothelial cell proliferation. The invention also relates to pharmaceutical compositions containing analogs of troponin subunits C, I, or T and analogs of their fragments, in therapeutically effective amounts that are capable of inhibiting endothelial cell proliferation. The invention further relates to treatment of neovascular disorders by administration of a therapeutic compound of the invention.

5 Claims, 3 Drawing Sheets

OTHER PUBLICATIONS

Haudenschild et al., 1976, "Human vascular endothelial cells in culture", Exp Cell Res 98:175–183.

Langer et al., 1976, "Polymers for the sustained release of proteins and other macromolecules", Nature 263:797–800.

Lutty et al., 1983, "Vitreous: An inhibitor of retinal extract–induced neovascularization", Invest Ophthamol Vis Sci 24:52–56.

Moses et al., 1991, "Inhibitors of angiogenesis", Biotechnology 9:630–634.

Patz et al., 1982, "Clinical and experimental studies on retinal neovascularization", Am J Ophthamol 94:715–743.

Polverini et al., 1991, "Assay and purification of naturally occuring inhibitor of angiogenesis", Meth Enzymol 198:440–450.

Rastinejad et al., 1989, "Regulation of the activity of a new inhibitor of angiogenesis by a cancer suppressor gene", Cell 56:345–355.

Schreier et al., 1990, "Cloning, structural analysis, and expression of the human slow twitch skeletal muscle/cardiac troponin C gene", J Biol Chem 265:21247–21253.

Shaub et al; 1969, "The relaxing protein system of striated muscle", Biochem J 115:993.

Shing et al., 1984, "Heparin affinity: Purification of a tumor–derived capillary endothelial cell growth factor", Science 223:1296–1299.

Taylor and Folkman, 1982, "Protamine is an inhibitor of angiogenesis", Nature 297:307–312.

Teicher et al., 1994, "Potentiation of cytotoxic cancer therapies by TNP–470 alone and with other anti–angiogenic agents", Int J Cancer 57:920–925.

Waltman et al., 1978, "Choroidal nowvascularization associated with choroidal nevi", Am J Ophthamol 85:704–710.

Wu et al., 1994, "Isolation and characterization of human fast skeletal β troponin T cDNA: Comparative sequence analysis of isoforms and insight into the evolution of members of a multigene family", DNA Cell Biol 13:217–233.

Xu and Hitchcock–DeGregori, 1988, "Synthesis of a troponin C cDNA and expression of wild–type and mutant proteins in *Escherichia coli*", J Biol Chem 263:13962–13969.

Yasui et al., 1968, "The role of the sulfhydryl groups of tropomyosin and troponin in the calcium control of actomyosin contractility", J Biol Chem 243:735–742.

Yates and Greaser, 1983, "Troponin subunit stoichiometry and content in rabbit skeletal muscle and myofibrils", J Biol Chem 258:5770–5774.

Tanokura, M. et al. Interactions among chymotryptic troponin T subfragments, tropomyosin, troponin I and troponin C. J. Biochem. (Tokyo), 95(5), 1417–21, Jan. 1984.

Garabarek, Z. et al. Proteolytic fragments of troponin C interactions with the other troponin subunits and biological activity. J. Biol Chem 256 (24) 13121–13127, Jan. 1981.

Morris E.P. et al.Troponin tropomyosin interaction fluorescent studies of the binding of troponin T and chimotryptic troponin T fragments to specificallylabeled tropomyosin. Biochemistry 23 (10), 2214–2220, Jan. 1981.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 160 amino acids
        ( B ) TYPE: amino acid
        ( C ) STRANDEDNESS: single
        ( D ) TOPOLOGY: linear ( i i ) MOLECULE TYPE: None ( i x ) FEATURE:
        ( A ) NAME/KEY: Peptide
        ( B ) LOCATION: 1..160
        ( D ) OTHER INFORMATION: /label=Human Fast Twitch Skeletal Muscle Troponin C ( x i ) SEQUENCE DESCRIPTION: SEQ ID NO:1:

```
Met  Thr  Asp  Gln  Gln  Ala  Glu  Ala  Arg  Ser  Tyr  Leu  Ser  Glu  Glu  Met
 1                  5                       10                       15

Ile  Ala  Glu  Phe  Lys  Ala  Ala  Phe  Asp  Met  Phe  Asp  Ala  Asp  Gly  Gly
                20                      25                       30

Gly  Asp  Ile  Ser  Val  Lys  Glu  Leu  Gly  Thr  Val  Met  Arg  Met  Leu  Gly
           35                      40                       45

Gln  Thr  Pro  Thr  Lys  Glu  Glu  Leu  Asp  Ala  Ile  Ile  Glu  Glu  Val  Asp
      50                      55                       60

Glu  Asp  Gly  Ser  Gly  Thr  Ile  Asp  Phe  Glu  Glu  Phe  Leu  Val  Met  Met
 65                      70                       75                       80

Val  Arg  Gln  Met  Lys  Glu  Asp  Ala  Lys  Gly  Lys  Ser  Glu  Glu  Glu  Leu
                85                      90                       95

Ala  Glu  Cys  Phe  Arg  Ile  Phe  Asp  Arg  Asn  Ala  Asp  Gly  Tyr  Ile  Asp
               100                     105                      110

Pro  Glu  Glu  Leu  Ala  Glu  Ile  Phe  Arg  Ala  Ser  Gly  Glu  His  Val  Thr
          115                     120                      125
```

-continued

| Asp | Glu | Glu | Ile | Glu | Ser | Leu | Met | Lys | Asp | Gly | Asp | Lys | Asn | Asn | Asp |
|---|---|---|---|---|---|---|---|---|---|---|---|---|---|---|---|
| | 130 | | | | 135 | | | | | 140 | | | | | |

| Gly | Arg | Ile | Asp | Phe | Asp | Glu | Phe | Leu | Lys | Met | Met | Glu | Gly | Val | Gln |
|---|---|---|---|---|---|---|---|---|---|---|---|---|---|---|---|
| 145 | | | | | 150 | | | | | 155 | | | | | 160 |

( 2 ) INFORMATION FOR SEQ ID NO:2:

( i ) SEQUENCE CHARACTERISTICS:
    ( A ) LENGTH: 182 amino acids
    ( B ) TYPE: amino acid
    ( C ) STRANDEDNESS: single
    ( D ) TOPOLOGY: linear ( i i ) MOLECULE TYPE: None ( i x ) FEATURE:
    ( A ) NAME/KEY: Peptide
    ( B ) LOCATION: 1..182
    ( D ) OTHER INFORMATION: /label=Human Fast Twitch Skeletal
          Muscle Troponin I ( x i ) SEQUENCE DESCRIPTION: SEQ ID NO:2:

| Met | Gly | Asp | Glu | Glu | Lys | Arg | Asn | Arg | Ala | Ile | Thr | Ala | Arg | Arg | Gln |
|---|---|---|---|---|---|---|---|---|---|---|---|---|---|---|---|
| 1 | | | | 5 | | | | | 10 | | | | | 15 | |

| His | Leu | Lys | Ser | Val | Met | Leu | Gln | Ile | Ala | Ala | Thr | Glu | Leu | Glu | Lys |
|---|---|---|---|---|---|---|---|---|---|---|---|---|---|---|---|
| | | | 20 | | | | | 25 | | | | | 30 | | |

| Glu | Glu | Ser | Arg | Arg | Glu | Ala | Glu | Lys | Gln | Asn | Tyr | Leu | Ala | Glu | His |
|---|---|---|---|---|---|---|---|---|---|---|---|---|---|---|---|
| | | 35 | | | | | 40 | | | | | 45 | | | |

| Cys | Pro | Pro | Leu | His | Ile | Pro | Gly | Ser | Met | Ser | Glu | Val | Gln | Glu | Leu |
|---|---|---|---|---|---|---|---|---|---|---|---|---|---|---|---|
| | 50 | | | | | 55 | | | | | 60 | | | | |

| Cys | Lys | Gln | Leu | His | Ala | Lys | Ile | Asp | Ala | Ala | Glu | Glu | Glu | Lys | Tyr |
|---|---|---|---|---|---|---|---|---|---|---|---|---|---|---|---|
| 65 | | | | | 70 | | | | | 75 | | | | | 80 |

| Asp | Met | Glu | Val | Arg | Val | Gln | Lys | Thr | Ser | Lys | Glu | Leu | Glu | Asp | Met |
|---|---|---|---|---|---|---|---|---|---|---|---|---|---|---|---|
| | | | | 85 | | | | | 90 | | | | | 95 | |

| Asn | Gln | Lys | Leu | Phe | Asp | Leu | Arg | Gly | Lys | Phe | Lys | Arg | Pro | Pro | Leu |
|---|---|---|---|---|---|---|---|---|---|---|---|---|---|---|---|
| | | | 100 | | | | | 105 | | | | | 110 | | |

| Arg | Arg | Val | Arg | Met | Ser | Ala | Asp | Ala | Met | Leu | Lys | Ala | Leu | Leu | Gly |
|---|---|---|---|---|---|---|---|---|---|---|---|---|---|---|---|
| | | | 115 | | | | | 120 | | | | | 125 | | |

| Ser | Lys | His | Lys | Val | Cys | Met | Asp | Leu | Arg | Ala | Asn | Leu | Lys | Gln | Val |
|---|---|---|---|---|---|---|---|---|---|---|---|---|---|---|---|
| | 130 | | | | | 135 | | | | | 140 | | | | |

| Lys | Lys | Glu | Asp | Thr | Glu | Lys | Glu | Arg | Asp | Leu | Arg | Asp | Val | Gly | Asp |
|---|---|---|---|---|---|---|---|---|---|---|---|---|---|---|---|
| 145 | | | | | 150 | | | | | 155 | | | | | 160 |

| Trp | Arg | Lys | Asn | Ile | Glu | Glu | Lys | Ser | Gly | Met | Glu | Gly | Arg | Lys | Lys |
|---|---|---|---|---|---|---|---|---|---|---|---|---|---|---|---|
| | | | | 165 | | | | | 170 | | | | | 175 | |

| Met | Phe | Glu | Ser | Glu | Ser |
|---|---|---|---|---|---|
| | | | 180 | | |

( 2 ) INFORMATION FOR SEQ ID NO:3:

( i ) SEQUENCE CHARACTERISTICS:
    ( A ) LENGTH: 258 amino acids
    ( B ) TYPE: amino acid
    ( C ) STRANDEDNESS: single
    ( D ) TOPOLOGY: linear ( i i ) MOLECULE TYPE: None ( i x ) FEATURE:
    ( A ) NAME/KEY: Peptide
    ( B ) LOCATION: 1..258
    ( D ) OTHER INFORMATION: /label=Human Fast Skeletal Beta
          Troponin T ( x i ) SEQUENCE DESCRIPTION: SEQ ID NO:3:

-continued

```
Met  Ser  Asp  Glu  Glu  Val  Glu  Gln  Val  Glu  Glu  Gln  Tyr  Glu  Glu  Glu
 1              5                        10                      15
Glu  Glu  Ala  Gln  Glu  Glu  Glu  Glu  Val  Gln  Glu  Asp  Thr  Ala  Glu  Glu
               20                        25                      30
Asp  Ala  Glu  Glu  Glu  Lys  Pro  Arg  Pro  Lys  Leu  Thr  Ala  Pro  Lys  Ile
          35                   40                      45
Pro  Glu  Gly  Glu  Lys  Val  Asp  Phe  Asp  Asp  Ile  Gln  Lys  Lys  Arg  Gln
     50                        55                 60
Asn  Lys  Asp  Leu  Met  Glu  Leu  Gln  Ala  Leu  Ile  Asp  Ser  His  Phe  Glu
 65                      70                  75                           80
Ala  Arg  Lys  Lys  Glu  Glu  Glu  Leu  Val  Ala  Leu  Lys  Glu  Arg  Ile
                    85                  90                      95
Glu  Lys  Arg  Arg  Ala  Glu  Arg  Ala  Glu  Gln  Gln  Arg  Ile  Arg  Ala  Glu
               100                 105                      110
Lys  Glu  Arg  Glu  Arg  Gln  Asn  Arg  Leu  Ala  Glu  Glu  Lys  Ala  Arg  Arg
          115                 120                 125
Glu  Glu  Glu  Asp  Ala  Lys  Arg  Arg  Ala  Glu  Asp  Asp  Leu  Lys  Lys  Lys
     130                 135                 140
Lys  Ala  Leu  Ser  Ser  Met  Gly  Ala  Asn  Tyr  Ser  Ser  Tyr  Leu  Ala  Lys
145                      150                 155                           160
Ala  Asp  Gln  Lys  Arg  Gly  Lys  Lys  Gln  Thr  Ala  Arg  Glu  Met  Lys  Lys
                    165                 170                      175
Lys  Ile  Leu  Ala  Glu  Arg  Arg  Lys  Pro  Leu  Asn  Ile  Asp  His  Leu  Gly
               180                 185                      190
Glu  Asp  Lys  Leu  Arg  Asp  Lys  Ala  Lys  Glu  Leu  Trp  Glu  Thr  Leu  His
          195                 200                 205
Gln  Leu  Glu  Ile  Asp  Lys  Phe  Glu  Phe  Gly  Glu  Lys  Leu  Lys  Arg  Gln
     210                      215                 220
Lys  Tyr  Asp  Ile  Thr  Thr  Leu  Arg  Ser  Arg  Ile  Asp  Gln  Ala  Gln  Lys
225                      230                 235                           240
His  Ser  Lys  Lys  Ala  Gly  Thr  Pro  Ala  Lys  Gly  Lys  Val  Gly  Gly  Arg
                    245                 250                 255
Trp  Lys
```

PHARMACEUTICAL COMPOSITIONS COMPRISING TROPONIN SUBUNITS, FRAGMENTS AND ANALOGS THEREOF AND METHODS OF THEIR USE TO INHIBIT ANGIOGENESIS

The present invention provides for a novel pharmaceutical composition, and method of use thereof for the treatment of diseases or disorders involving abnormal angiogenesis.

More particularly, the present invention is based, in part, on the discovery that troponin subunits C, I and T inhibit stimulated endothelial cell proliferation. Pharmaceutical compositions containing therapeutically effective amounts of troponin C, I, or T, subunits, fragments, or analogs and methods of therapeutic use thereof are provided.

BACKGROUND

Angiogenesis, the process of new blood vessel development and formation, plays an important role in numerous physiological events, both normal and pathological. Angiogenesis occurs in response to specific signals and involves a complex process characterized by infiltration of the basal lamina by vascular endothelial cells in response to angiogenic growth signal(s), migration of the endothelial cells toward the source of the signal(s), and subsequent proliferation and formation of the capillary tube. Blood flow through the newly formed capillary is initiated after the endothelial cells come into contact and connect with a preexisting capillary.

The naturally occurring balance between endogenous stimulators and inhibitors of angiogenesis is one in which inhibitory influences predominate. Rastinejad et al., 1989, *Cell* 56:345–355. In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., 1991, *Biotech.* 9:630–634; Folkman et al., 1995, *N. Engl. J. Med.,* 333:1757–1763; Auerbach et al., 1985, *J. Microvasc. Res.* 29:401–411; Folkman, 1985, Advances in Cancer Research, eds. Klein and Weinhouse, Academic Press, New York, pp. 175–203; Patz, 1982, *Am. J. Opthalmol.* 94:715–743; and Folkman et al., 1983, *Science* 221:719–725. In a number of pathological conditions, the process of angiogenesis contributes to the disease state. For example, significant data have accumulated which suggest that the growth of solid tumors is dependent on angiogenesis. Folkman and Klagsbrun, 1987, *Science* 235:442–447.

The maintenance of the avascularity of the cornea, lens, and trabecular meshwork is crucial for vision as well as to ocular physiology. There are several eye diseases, many of which lead to blindness, in which ocular neovascularization occurs in response to the diseased state. These ocular disorders include diabetic retinopathy, neovascular glaucoma, inflammatory diseases and ocular tumors (e.g., retinoblastoma). There are also a number of other eye diseases which are also associated with neovascularization, including retrolental fibroplasia, uveitis, retinopathy of prematurity, macular degeneration, and approximately twenty eye diseases which are associated with choroidal neovascularization and approximately forty eye diseases associated with iris neovascularization. See, e.g., reviews by Waltman et al., 1978, *Am. J. Ophthal.* 85:704–710 and Gartner et al., 1978, *Surv. Ophthal.* 22:291–312. Currently, the treatment of these diseases, especially once neovascularization has occurred, is inadequate and blindness often results. Studies have suggested that vaso-inhibitory factors which are present in normal ocular tissue (cornea and vitreous) are lost in the diseased state.

An inhibitor of angiogenesis could have an important therapeutic role in limiting the contributions of this process to pathological progression of the underlying disease states as well as providing a valuable means of studying their etiology. For example, agents that inhibit tumor neovascularization could play an important role in inhibiting metastatic tumor growth.

The components of angiogenesis relating to vascular endothelial cell proliferation, migration and invasion, have been found to be regulated in part by polypeptide growth factors. Experiments in culture, indicate that endothelial cells exposed to a medium containing suitable growth factors can be induced to evoke some or all of the angiogenic responses. Several polypeptides with in vitro endothelial growth promoting activity have been identified. Examples include acidic and basic fibroblast growth factors, transforming growth factors α and β, platelet-derived endothelial cell growth factor, granulocyte colony-stimulating factor, interleukin-8, hepatocyte growth factor, proliferin, vascular endothelial growth factor and placental growth factor. See, e.g., review by Folkman et al., 1995, *N. Engl. J. Med.,* 333:1757–1763.

Although extracts from several different tissue sources have been shown to contain anti-angiogenic activity, several molecules such as platelet factor-4, thrombospondin, protamine, and transforming growth factor B, have been found to negatively regulate different aspects of angiogenesis, such as cell proliferation or cell migration, no single tissue-derived macromolecule capable of inhibiting angiogenesis has been identified in the prior art. See, e.g., reviews by Folkman, J., 1995, *N. Engl. J. Med.* 333:1757–1763 and D'Amore, 1985, *Prog. Clin. Biol. Res.* 221:269–283. There is therefore a great need for the further identification and characterization of chemical agents which can prevent the continued deregulated spread of vascularization and which would potentially have broad applicability as a therapy for those diseases in which neovascularization plays a prominent role.

Capillary endothelial cells ("EC") proliferate in response to an angiogenic stimulus during neovascularization. Ausprunk and Folkman, 1977, *J. Microvasc. Res.* 14:153–65. An in vitro assay assessing endothelial cell proliferation in response to known angiogenesis simulating factors, such as acidic or basic fibroblast growth factor (aFGF and bFGF, respectively), has been developed to mimic the process of neovascularization in vitro. This type of assay is the assay of choice to demonstrate the stimulation of capillary EC proliferation by various angiogenic factors. Shing et al., 1984, *Science* 223:1296–1298.

The process of capillary EC migration through the extracellular matrix towards an angiogenic stimulus is also a critical event required for angiogenesis. See, e.g., review by Ausprunk et al., 1977, *J. Microvasc. Res.* 14:53–65. This process provides an additional assay by which to mimic the process of neovascularization in vitro. A modification of the Boyden chamber technique has been developed to monitor EC migration. Boyden et al., 1962, *J. Exptl. Med.* 115:453–456, Example 4. To date, only a few tissue-derived EC cell migration inhibitors are known. See, e.g., review by Langer et al., 1976, *Science* 193:70–72.

In the early 1970's, a number of in vivo angiogenesis model bioassays were widely used. These model systems included rabbit corneal pocket, chick chorioallantoic membrane ("CAM"), rat dorsal air sac and rabbit air chamber bioassays. For review, see, Blood et al., 1990, *Biochem. et Biophys. Acta* 1032:89–118. The development of controlled release polymers capable of releasing large molecules such as angiogenesis stimulators and inhibitors was critical to the use of these assays. Langer et al., 1976, *Nature* 263:797–800.

In the CAM bioassay, fertilized chick embryos are cultured in Petri dishes On day 6 of development, a disc of a release polymer, such as methyl cellulose, impregnated with the test sample or an appropriate control substance is placed onto the vascular membrane at its advancing edge. On day 8 of development, the area around the implant is observed and evaluated. Avascular zones surrounding the test implant indicate the presence of an inhibitor of embryonic neovascularization. Moses et al., 1990, *Science*, 248:1408–1410 and Taylor et al., 1982, *Nature*, 297:307–312. The reported doses for previously described angiogenesis inhibitors tested alone in the CAM assay are 50 μg of protamine (Taylor et al. (1982)), 200 μg of bovine vitreous extract (Lutty et al., 1983, *Invest. Opthalmol. Vis. Sci.* 24:53–56), and 10 μg of platelet factor IV (Taylor et al. (1982)). The lowest reported doses of angiogenesis inhibitors effective as combinations include heparin (50 μg) and hydrocortisone (60 μg), and B-cyclodextrin tetradecasulfate (14 μg) and hydrocortisone (60 μg), reported by Folkman et al., 1989, *Science* 243:1490.

According to the rabbit corneal pocket assay, polymer pellets of ethylene vinyl acetate copolymer ("EVAC") are impregnated with test substance and surgically implanted in a pocket in the rabbit cornea approximately 1 mm from the limbus. Langer et al., 1976, *Science* 193:707–72. To test for an angiogenesis inhibitor, either a piece of carcinoma or some other angiogenic stimulant is implanted distal to the polymer 2 mm from the limbus. In the opposite eye of each rabbit, control polymer pellets that are empty are implanted next to an angiogenic stimulant in the same way. In these control corneas, capillary blood vessels start growing towards the tumor implant in 5–6 days, eventually sweeping over the blank polymer. In test corneas, the directional growth of new capillaries from the limbal blood vessel towards the tumor occurs at a reduced rate and is often inhibited such that an avascular region around the polymer is observed. This assay is quantitated by measurement of the maximum vessel lengths with a stereospecific microscope.

Troponin, a complex of three polypeptides is an accessory protein that is closely associated with actin filaments in vertebrate muscle. The troponin complex, acts in conjunction with the muscle form of tropomyosin to mediate the $Ca^{2+}$ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponins I and T, and tropomyosin, inhibits the interaction of actin and myosin. Troponin C is capable of binding up to four calcium molecules. Studies suggest that when the level of calcium in the muscle is raised, troponin C causes troponin I to loose its hold on the actin molecule, causing the tropomyosin molecule shift, thereby exposing the myosin binding sites on actin and stimulating myosin ATPase activity. Prior to the discovery of the present invention, troponin subunits were not known to inhibit the process of endothelial cel proliferation.

The citation of a reference herein shall not be construed as an admission that such reference is prior art to the present invention.

SUMMARY OF THE INVENTION

The present invention relates to pharmaceutical compositions containing troponin subunits C, I, or T, or fragments thereof, in therapeutically effective amounts that are capable of inhibiting endothelial cell proliferation. The invention also relates to pharmaceutical compositions containing analogs of troponin subunits C, I, or T and analogs of their fragments, in therapeutically effective amounts that are capable of inhibiting endothelial cell proliferation. The invention further relates to treatment of neovascular disorders by administration of a therapeutic compound of the invention. Such therapeutic compounds (termed herein "Therapeutics"), include: troponin subunits C, I, and T, and fragments and analogs thereof. In one embodiment, a Therapeutic of the invention is administered to treat a cancerous condition, or to prevent progression from the pre-neoplastic or pre-malignant state into a neoplastic or a malignant state. In other specific embodiments, a Therapeutic of the invention is administered to treat ocular disorders associated with neovascularization.

Definitions

As used herein,:

The term "troponin subunit", when not preceding the terms C, I or T, means generically any of troponin subunits C, I, or T.

DETAILED DESCRIPTION OF THE INVENTION

Figure 1:
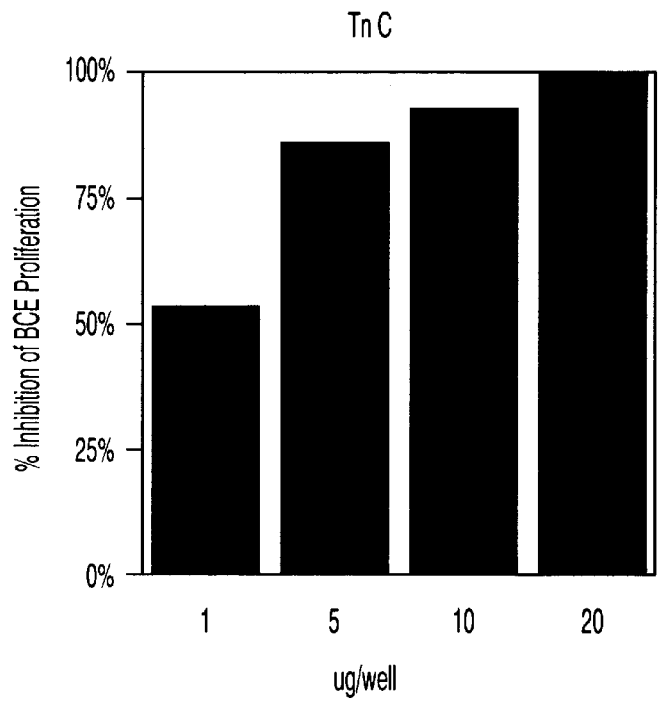
FIG. 1. Inhibition of bovine capillary Endothelial Cell (BCE) proliferation by troponin C. Percent inhibition of bFGF-stimulated BCE proliferation is shown as a function of troponin C concentration (nM). Percent inhibition was determined by comparing results obtained for cells treated with stimulus alone with those obtained for samples exposed to both stimulus and inhibitor. Well volume was 200 μl.

The present invention relates to therapeutic methods and compositions based on troponin subunits. The invention provides for treatment of neovascular disorders by administration of a therapeutic compound of the invention. Such therapeutic compounds (termed herein "Therapeutics") include: troponin C, I, and T subunits, fragments and analogs thereof (collectively "peptides of the invention"). The peptides of the invention are characterized by the property of inhibiting bovine endothelial cell proliferation in culture with an $IC_{50}$ of 10 μM or less. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat an ocular disorder associated with neovascularization.

In a preferred aspect, a Therapeutic of the invention is a peptide consisting of at least a fragment of troponin C, troponin I, troponin T, or troponins C and I, which is effective to inhibit endothelial cell proliferation.

Examples of the troponin subunits that can be utilized in accordance with the invention, include the subunits of troponin from human fast twitch skeletal muscle, the sequences of which are given below:

embodiment, the amino acid sequence of the peptide has at least 80% identity compared to the fragment of human fast-twitch skeletal troponin C from which it is derived (the "prototype fragment"). In another embodiment, this identity is greater than 85%. In a more preferred embodiment, this identity is greater than 90%. In a most preferred embodiment, the amino acid sequence of the peptide has at least 95% identity with the prototype fragment. Fragments can be at least 10 amino acids, and in preferred embodiments at least 50, 75, 100 and 120 amino acids, respectively.

In another embodiment, the invention encompasses peptides which are homologous to human fast-twitch skeletal troponin I(SEQ ID NO:2) or fragments thereof. In one embodiment, the amino acid sequence of the peptide has at least 80% identity with the prototype human fast-twitch skeletal troponin I fragment. In another embodiment, this identity is greater than 85%. In a more preferred embodiment, this identity is greater than 90%. In a most preferred embodiment, the amino acid sequence of the peptide has at least 95% identity with the prototype fragment. Fragments can be at least 10 amino acids, and in preferred embodiments at least 50, 75, 100 and 120 amino acids, respectively.

In another embodiment, the invention encompasses peptides which are homologous to human fast-twitch skeletal troponin T (SEQ ID NO:3) or fragments thereof. In one embodiment, the amino acid sequence of the peptide has at least 80% identity with the prototype human fast-twitch skeletal beta troponin T. In another embodiment, this identity is greater than 85%. In a more preferred embodiment, Human Fast Twitch Skeletal Muscle Troponin C (SEQ ID NO:1)

| | | | | | | | | | | | | | | | | | | | | |
|---|---|---|---|---|---|---|---|---|---|---|---|---|---|---|---|---|---|---|---|---|
| 1 | M | T | D | Q | Q | A | E | A | R | S | Y | L | S | E | E | M | I | A | E | F |
| 21 | K | A | A | F | D | M | F | D | A | D | G | G | G | D | I | S | V | K | E | L |
| 41 | G | T | V | M | R | M | L | G | Q | T | P | T | K | E | E | L | D | A | I | I |
| 61 | E | E | V | D | E | D | G | S | G | T | I | D | F | E | E | F | L | V | M | M |
| 81 | V | R | Q | M | K | E | D | A | K | G | K | S | E | E | E | L | A | E | C | F |
| 101 | R | I | F | D | R | N | A | D | G | Y | I | D | P | E | E | L | A | E | I | F |
| 121 | R | A | S | G | E | H | V | T | D | E | E | I | E | S | L | M | K | D | G | D |
| 141 | K | N | N | D | G | R | I | D | F | D | E | F | L | K | M | M | E | G | V | Q |

Human Fast Twitch Skeletal Muscle Troponin I (SEQ ID NO:2)

| | | | | | | | | | | | | | | | | | | | | |
|---|---|---|---|---|---|---|---|---|---|---|---|---|---|---|---|---|---|---|---|---|
| 1 | M | G | D | E | E | K | R | N | R | A | I | T | A | R | R | Q | H | L | K | S |
| 21 | V | M | L | Q | I | A | A | T | E | L | E | K | E | E | S | R | R | E | A | E |
| 41 | K | Q | N | Y | L | A | E | H | C | P | P | L | H | I | P | G | S | M | S | E |
| 61 | V | Q | E | L | C | K | Q | L | H | A | K | I | D | A | A | E | E | E | K | Y |
| 81 | D | M | E | V | R | V | Q | K | T | S | K | E | L | E | D | M | N | Q | K | L |
| 101 | F | D | L | R | G | K | F | K | R | P | P | L | R | R | V | R | M | S | A | D |
| 121 | A | M | L | K | A | L | L | G | S | K | H | K | V | C | M | D | L | R | A | N |
| 141 | L | K | Q | V | K | K | E | D | T | E | K | E | R | D | L | R | D | V | G | D |
| 161 | W | R | K | N | I | E | E | K | S | G | M | E | G | R | K | K | M | F | E | S |
| 181 | E | S | | | | | | | | | | | | | | | | | | | |

Human Fast Skeletal Beta Troponin T (SEQ ID NO:3)

| | | | | | | | | | | | | | | | | | | | | |
|---|---|---|---|---|---|---|---|---|---|---|---|---|---|---|---|---|---|---|---|---|
| 1 | M | S | D | E | E | V | E | Q | V | E | E | Q | Y | E | E | E | E | E | A | Q |
| 21 | E | E | E | E | V | Q | E | D | T | A | E | E | D | A | E | E | E | K | P | R |
| 41 | P | K | L | T | A | P | K | I | P | E | G | E | K | V | D | F | D | D | I | Q |
| 61 | K | K | K | R | Q | N | K | D | L | M | E | L | Q | A | L | I | D | S | H | F | E |
| 81 | A | R | K | K | E | E | E | E | L | V | A | L | K | E | R | I | E | K | R | R |
| 101 | A | E | R | A | E | Q | Q | R | I | R | A | E | K | E | R | E | R | Q | N | R |
| 121 | L | A | E | E | K | A | R | R | E | E | E | D | A | K | R | R | A | E | D | D |
| 141 | L | K | K | K | K | A | L | S | S | M | G | A | N | Y | S | S | Y | L | A | K |
| 161 | A | D | Q | K | R | G | K | K | Q | T | A | R | E | M | K | K | K | I | L | A |
| 181 | E | R | R | K | P | L | N | I | D | H | L | G | E | D | K | L | R | D | K | A |
| 201 | K | E | L | W | E | T | L | H | Q | L | E | I | D | K | F | E | F | G | E | K |
| 221 | L | K | R | Q | K | Y | D | I | T | T | L | R | S | R | I | D | Q | A | Q | K |
| 241 | H | S | K | K | A | G | T | P | A | K | G | K | V | G | G | R | W | K | | | |

In another embodiment, the invention encompasses peptides which are homologous to human fast-twitch skeletal troponin C (SEQ ID NO:1) or fragments thereof. In one this identity is greater than 90%. In a most preferred embodiment, the amino acid sequence of the peptide has at least 95% identity with the prototype fragment. Fragments can be at least 10 amino acids, and in preferred embodiments at least 50, 75, 100, 120 and 200 amino acids in length, respectively.

In other specific embodiments, the peptides of the invention are troponin C, troponin I and troponin T subunits of the fast twitch, slow twitch and cardiac isoforms from other mammalian species, e.g., human, rabbit, rat, mouse, bovine, ovine and porcine.

In a specific embodiment, a Therapeutic of the invention is combined with a therapeutically effective amount of another molecule which negatively regulates angiogenesis which may be, but is not limited to, platelet factor 4, thrombospondin-1, tissue inhibitors of metalloproteases (TIMP1 and TIMP2) prolactin (16-Kd fragment), angiostatin (38-Kd fragment of plasminogen), bfGf soluble receptor, transforming growth factor β, interferon alfa, and placental proliferin-related protein.

Paradoxically, neovascularization gradually reduces a tumors accessibility to chemotherapeutic drugs due to increased interstitial pressure within the tumor, which causes vascular compression and central necrosis. In vivo results have demonstrated that rodents receiving angiogenic therapy show increased delivery of chemotherapy to a tumor. Teicher et al., 1994, *Int. J. Cancer* 57:920–925. Thus, in one embodiment, the invention provides for a pharmaceutical composition of the present invention in combination with a chemotherapeutic agent.

In another preferred aspect, a Therapeutic of the invention is combined with chemotherapeutic agents or radioactive isotope exposure.

The invention is illustrated by way of examples infra which disclose, inter alia, the inhibition of capillary endothelial cell proliferation by troponin subunits C, I, and T and the means for determining inhibition of capillary endothelial cell migration and inhibition of neovascularization in vivo by troponin subunits.

For clarity of disclosure, and not by way of limitation, the detailed description of the invention is divided into the subsections set forth below.

TROPONIN SUBUNITS, Fragments AND ANALOGS

The invention provides for pharmaceutical compositions comprising troponin subunits, fragments, and analogs thereof. In particular aspects, the subunits, fragments, or analogs are of fly, frog, mouse, rat, rabbit, pig, cow, dog, monkey, or human troponin subunits.

It is envisioned that troponin subunit fragments can be made by altering troponin sequences by substitutions, additions or deletions that provide for functionally equivalent molecules. These include, but are not limited to, troponin subunits, fragments, or analogs containing, as a primary amino acid sequence, all or part of the amino acid sequence of a troponin subunit including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

One embodiment of the invention provides for molecules consisting of or comprising a fragment of at least 10 (continuous) amino acids of a troponin subunit which is capable of inhibiting endothelial cell proliferation. In other embodiments, this molecule consists of at least 20 or 50 amino acids of the troponin subunit. In specific embodiments, such molecules consist of or comprise fragments of a troponin subunit that at least 75, 120 or 200 amino acids.

In a preferred embodiment, the protein is a mammalian troponin subunit. In alternative embodiments, it is a mammalian troponin C, I, or T subunit.

The troponin subunit fragments and analogs of the invention can be derived from tissue (see, for example, Example 1; Ebashi et al., 1968, *J. Biochem.* 64:465; Yasui et al., 1968, *J. Biol. Chem.* 243:735; Hartshorne et al., 1968, *Biochem. Biophys. Res. Commun.* 31:647; Shaub et al., 1969, *Biochem. J.* 115:993; Greaser et al., 1971, *J. Biol. Chem.* 246:4226–4733; Brekke et al., 1976, *J. Biol. Chem.* 251:866–871; and Yates et al., 1983, *J. Biol. Chem.* 258:5770–5774) or produced by various methods known in the art. The manipulations which result in their production can occur at the gene or protein level. For example, a cloned troponin gene sequence coding for troponin subunits C, I, or T, can be modified by any of numerous strategies known in the art. Sambrook et al., 1990, Molecular Cloning, A Laboratory Manual, 2d ed., Cold Spring Harbor Laboratory, Cold Spring Harbor, N.Y. The sequence can be cleaved at appropriate sites with restriction endonuclease(s), followed by further enzymatic modification if desired, isolated, and ligated in vitro. In the production of the gene encoding a derivative or analog of a troponin subunit, care should be taken to ensure that the modified gene remains within the same translational reading frame as the troponin subunit gene, uninterrupted by translational stop signals, in the gene region where the desired troponin activity is encoded.

Additionally, the troponin subunit encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including, but not limited to, in vitro site-directed mutagenesis (Hutchinson et al., 1978, *J. Biol. Chem.* 253:6551), use of TAB® linkers (Pharmacia), etc.

Manipulations of troponin subunit C, I, or T sequence may also be made at the protein level. Included within the scope of the invention are troponin subunit fragments or other fragments or analogs which are differentially modified during or after translation, e.g., by acetylation, phosphorylation, carboxylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, $NaBH_4$, acetylation, formylation, oxidation, reduction, etc.

In addition, fragments and analogs of troponin subunits can be chemically synthesized. For example, a peptide corresponding to a portion of a troponin subunit which comprises the desired domain, or which mediates the desired activity in vitro, can be synthesized by use of a peptide synthesizer. Furthermore, if desired, nonclassical amino acids or chemical amino acid analogs can be introduced as a substitution or addition into the troponin subunit sequence. Non-classical amino acids include, but are not limited to, the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the invention encompasses a chimeric, or fusion, protein comprising a troponin subunit or fragment thereof (consisting of at least a domain or motif of the troponin subunit that is responsible for inhibiting endothelial cell proliferation) joined at its amino or carboxy-terminus via a peptide bond to an amino acid sequence of a different protein. Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

ASSAYS OF TROPONIN PROTEINS FRAGMENTS AND ANALOGS

The functional activity and/or therapeutically effective dose of troponin subunits, fragments and analogs, can be assayed in vitro by various methods. These methods are based on the physiological processes involved in angiogenesis and while they are within the scope of the invention, they are not intended to limit the methods by which troponin subunits, fragments and analogs inhibiting angiogenesis are defined and/or a therapeutically effective dosage of the pharmaceutical composition is determined.

For example, where one is assaying for the ability of troponin subunits, fragments, and analogs, to inhibit or interfere with the proliferation of capillary endothelial cells (EC) in vitro, various bioassays known in the art can be used, including, but not limited to, radioactive incorporation into nucleic acids, calorimetric assays and cell counting.

Inhibition of endothelial cell proliferation may be measured by calorimetric determination of cellular acid phosphatase activity or electronic cell counting. These methods provide a quick and sensitive screen for determining the number of endothelial cells in culture after treatment with the troponin subunit, derivative, or analog of the invention, and an angiogenesis stimulating factor such as aFGF. The calorimetric determination of cellular acid phosphatase activity is described by Connolly et al., 1986, *J. Anal. Biochem.* 152:136–140. According to this method, described in Example 3, capillary endothelial cells are treated with angiogenesis stimulating factors, such as aFGF, and a range of potential inhibitor concentrations. These samples are incubated to allow for growth, and then harvested, washed, lysed in a buffer containing a phosphatase substrate, and then incubated a second time. A basic solution is added to stop the reaction and color development is determined at 405 λ. According to Connolly et al., a linear relationship is obtained between acid phosphatase activity and endothelial cell number up to 10,000 cells/sample. Standard curves for acid phosphatase activity are also generated from known cell numbers in order to confirm that the enzyme levels reflect the actual EC numbers. Percent inhibition is determined by comparing the cell number of samples exposed to stimulus with those exposed to both stimulus and inhibitor.

Colorimetric assays to determine the effect of troponin subunits C, I, and T on endothelial cell proliferation demonstrate that all three troponin subunits interefere with bFGF-stimulated endothelial cell proliferation.

Troponin C inhibited bFGF-stimulated endothelial cell proliferation in a dose-dependent manner in all concentrations tested (FIG. 1). Percent inhibition of bovine endothelial cell proliferation ("BCE" ) was 54%, 86%, 83%, and 100% at concentrations of 280 nM, 1.4 μm, 2.8 μM and 5.6 μM, respectively. An inhibition of 100% was observed at a concentration of 20 μg/well (5.6 μM). $IC_{50}$ represents the concentration at which 50% inhibition of aFGF growth factor-induced stimulation was observed. The $IC_{50}$ of troponin C was determined to be 278 nM.

Troponin I inhibited bFGF-stimulated BCE proliferation at concentrations of 1 and 5 μg/well, but inhibition was not observed in the sample tested at 10 μg/well (FIG. 2). The percent inhibition of BCE was 33% and 46% at concentrations of 240 nM and 1.2 μM, respectively. The $IC_{50}$of troponin I was determined to be 1.14 μM.

Troponin T inhibited bFGF-stimulated EC proliferation at concentrations of 10 and 20 ug/well, but not at concentrations of 1 and 5 μg/well (FIG. 3). BCE proliferation was inhibited 23% and 62% at 1.6 μM and 3.3 μM, respectively. The $IC_{50}$ of troponin T was determined to be 2.14 μM.

The combination of troponin subunits C and I inhibited EC at all concentrations tested (FIG. 4). The percent inhibition of BCE was 52%, 54% 73% and 47% at 130 nM, 645 nM, 1.3 μM and 2.6 μM, respectively. The $IC_{50}$ of this combination was determined to be 110 nM.

The combination of troponin subunits C, I and T was observed to inhibit aFGF stimulated BCE proliferation by 16% at a concentration of 360 nM (5 ug/well, FIG. 5).

The troponins samples tested had no detectable inhibitory effect on the growth of Balb/c 3T3 cells, a non-endothelial cell type.

The incorporation of radioactive thymidine by capillary endothelial cells represents another means by which to assay for the inhibition of endothelial cell proliferation by a potential angiogenesis inhibitor. According to this method, a predetermined number of capillary endothelial cells are grown in the presence of $^3$H-Thymidine stock, an angiogenesis stimulator such as for example, bFGF, and a range of concentrations of the angiogenesis inhibitor to be tested. Following incubation, the cells are harvested and the extent of thymidine incorporation is determined. See, Example 2.

The ability of varying concentrations of troponin subunits, fragments or analogs to interfere with the process of capillary endothelial cell migration in response to an angiogenic stimulus can be assayed using the modified Boyden chamber technique. See, Section 2 and Example 4, infra.

Another means by which to assay the functional activity of troponin subunits, fragments and analogs, involves examining the ability of the compounds to inhibit the directed migration of capillary endothelial cells which ultimately results in capillary tube formation. This ability may be assessed for example, using an assay in which capillary endothelial cells plated on collagen gels are challenged with the inhibitor, and determining whether capillary-like tube structures are formed by the cultured endothelial cells.

Assays for the ability to inhibit angiogenesis in vivo include the chick chorioallantoic membrane assay (see Section 2 and Example 5, infra) and rat or rabbit corneal pocket assays. See, Polverini et al., 1991, *Methods Enzymol.* 198:440–450. According to the corneal pocket assays, a tumor of choice is implanted into the cornea of the test animal in the form of a corneal pocket. The potential angiogenesis inhibitor is applied to the corneal pocket and the corneal pocket is routinely examined for neovascularization. See, Section 2 and Example 6 infra.

One embodiment of the invention provides for combination of the troponin subunits, fragments, or analogs of the present invention to inhibit angiogenesis. Another embodiment provides for the combination of troponin subunits, fragments, or analogs with other angiogenesis inhibiting factors. Such angiogenesis inhibiting factors include, but are not limited to: angiostatic steroids, thrombospondin, platelet factor IV, transforming growth factor β, interferons, tumor necrosis factor α, bovine vitreous extract, protamine, tissue inhibitors of metalloproteinases (TIMP-1 and TIMP-2), prolactin (16-kd fragment), angiostatin (38-kd fragment of plasminogen), bfGf soluble receptor, and placental proliferin-related protein. See, e.g., reviews by Folkman et al., 1995, *N. Engl. J. Med.* 333:1757–1763 and Klagsbrun et al., 1991, *Annu. Rev. Physiol.* 53:217–239.

The therapeutically effective dosage for inhibition of angiogenesis in vivo, defined as inhibition of capillary endothelial cell proliferation, migration, and/or blood vessel ingrowth, may be extrapolated from in vi tro inhibition assays using the compositions of the invention above or in combination with other angiogenesis inhibiting factors. The effective dosage is also dependent on the method and means of delivery. For example, in some applications, as in the treatment of psoriasis or diabetic retinopathy, the inhibitor is delivered in a topical-ophthalmic carrier. In other applications, as in the treatment of solid tumors, the inhibitor is delivered by means of a biodegradable, polymeric implant. The protein can also be modified, for example, by polyethyleneglycol treatment.

THERAPEUTIC USES

The invention provides for treatment of diseases or disorders associated with neovascularization by administration of a therapeutic compound of the invention. Such therapeutic compounds (termed herein "Therapeutics") include troponin subunits and fragments and analogs thereof (e.g., as described infra).

MALIGNANCIES

Malignant and metastatic conditions which can be treated with the Therapeutic compounds of the present invention include, but are not limited to, the solid tumors listed in Table 1 (for a review of such disorders, see Fishman et al., 1985, *Medicine,* 2d Ed., J. B. Lippincott Co., Philadelphia):

TABLE 1

MALIGNANCIES AND RELATED DISORDERS

Solid tumors sarcomas and carcinomas fibrosarcoma
myxosarcoma
liposarcoma
chondrosarcoma
osteogenic sarcoma
chordoma TABLE 1-continued

MALIGNANCIES AND RELATED DISORDERS

Solid tumors angiosarcoma
endotheliosarcoma
lymphangiosarcoma
lymphangioendotheliosarcoma
synovioma
mesothelioma
Ewing's tumor
leiomyosarcoma
rhabdomyosarcoma
colon carcinoma
pancreatic cancer
breast cancer
ovarian cancer
prostate cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
testicular tumor
lung carcinoma
small cell lung carcinoma
bladder carcinoma
epithelial carcinoma
glioma
astrocytoma
medulloblastoma
craniopharyngioma
ependymoma
Kaposi's sarcoma
pinealoma
hemangioblastoma
acoustic neuroma
oligodendroglioma
menangioma
melanoma
neuroblastoma
retinoblastoma

OCULAR DISORDERS

Ocular disorders associated with neovascularization which can be treated with the Therapeutic compounds of the present invention include, but are not limited to:

neovascular glaucoma
diabetic retinopathy
retinoblastoma
retrolental fibroplasia
uveitis
retinopathy of prematurity
macular degeneration
corneal graft neovascularization as well as other eye inflammatory diseases, ocular tumors and diseases associated with choroidal or iris neovascularization. See, e.g., reviews by Waltman et al., 1978, *Am. J. Ophthal.* 85:704–710 and Gartner et al., 1978, *Surv. Ophthal.* 22:291–312.

OTHER DISORDERS

Other disorders which can be treated with the Therapeutic compounds of the present invention include, but are not limited to, hemangioma, arthritis, psoriasis, angiofibroma, atherosclerotic plaques, delayed wound healing, granulations, hemophilic joints, hypertrophic scars, non-union fractures, Osler-Weber syndrome, pyogenic granuloma, scleroderma, trachoma, and vascular adhesions.

DEMONSTRATION OF THERAPEUTIC OR PROPHYLACTIC UTILITY

The Therapeutics of the invention can be tested in vivo for the desired therapeutic or prophylactic activity as well as for determination of therapeutically effective dosage. For example, such compounds can be tested in suitable animal model systems prior to testing in humans, including, but not limited to, rats, mice, chicken, cows, monkeys, rabbits, etc. For in vivo testing, prior to administration to humans, any animal model system known in the art may be used.

THERAPEUTIC/PROPHYLACTIC ADMINISTRATION AND COMPOSITIONS

The invention provides methods of treatment (and prophylaxis) by administration to a subject an effective amount of a Therapeutic of the invention. In a preferred aspect, the Therapeutic is substantially purified as set forth in Example 1. The subject is preferably an animal, including, but not limited to, animals such as cows, pigs, chickens, etc., and is preferably a mammal, and most preferably human.

The invention further provides methods of treatment by administration to a subject, an effective amount of a Therapeutic of the invention combined with a chemotherapeutic agent and/or radioactive isotope exposure.

The invention also provides for methods of treatment of a Therapeutic of the invention for patients who have entered a remission in order to maintain a dormant state.

Various delivery systems are known and can be used to administer a Therapeutic of the invention, e.g., encapsulation in liposomes, microparticles, microcapsules, receptor-mediated endocytosis (see, e.g., Wu and Wu, 1987, *J. Biol. Chem.* 262:4429–4432). Methods of introduction include, but are not limited to, topical, intradermal, intramuscular, intraperitoneal, intravenous, subcutaneous, intranasal, epidural, ophthalmic, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the purified troponin subunit is combined with a carrier so that an effective dosage is delivered, based on the desired activity (i.e., ranging from an effective dosage, for example, of 1.0 $\mu$M to 1.0 mM to prevent localized angiogenesis, endothelial cell migration, and/or inhibition of capillary endothelial cell proliferation. In one embodiment, a topical troponin subunit, fragment or analog is applied to the skin for treatment of diseases such as psoriasis. The carrier may in the form of, for example, and not by way of limitation, an ointment, cream, gel, paste, foam, aerosol, suppository, pad or gelled stick.

A topical Therapeutic for treatment of some of the eye disorders discussed infra consists of an effective amount of troponin subunit, fragment, or analog, in a ophthalmologically acceptable excipient such as buffered saline, mineral oil, vegetable oils such as corn or arachis oil, petroleum jelly, Miglyol 182, alcohol solutions, or liposomes or liposome-like products. Any of these compositions may also include preservatives, antioxidants, antibiotics, immunosuppressants, and other biologically or pharmaceutically effective agents which do not exert a detrimental effect on the troponin subunit.

For directed internal topical applications, for example for treatment of ulcers or hemorrhoids, the troponin subunit, fragment, or analog composition may be in the form of tablets or capsules, which can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

Suppositories generally contain active ingredient in the range of 0.5% to 10% by weight; oral formulations preferably contain 10% to 95% active ingredient.

In another embodiment, the Therapeutic can be delivered in a vesicle, in particular a liposome. See, Langer et al., 1990, *Science* 249:1527–1533; Treat et al., 1989, in Liposomes in the Therapy of Infectious Disease and Cancer, Lopez-Berestein and Fidler (eds.), Liss, N.Y., pp. 353 14 365; Lopez-Berestein, ibid., pp. 317–327.

In yet another embodiment, the Therapeutic can be delivered in a controlled release system. In one embodiment, an infusion pump may be used to administer troponin subunit, such as for example, that used for delivering insulin or chemotherapy to specific organs or tumors (see Langer, supra; Sefton, *CRC Crit. Ref. Biomed.,* 1987, Eng. 14:201; Buchwald et al., 1980, *Surgery* 88:507; Saudek et al., 1989, *N. Engl. J. Med.* 321:574.

In a preferred form, the troponin subunit, fragment, or analog is administered in combination with a biodegradable, biocompatible polymeric implant which releases the troponin subunit, fragment, or analog over a controlled period of time at a selected site. Examples of preferred polymeric materials include polyanhydrides, polyorthoesters, polyglycolic acid, polylactic acid, polyethylene vinyl acetate, and copolymers and blends thereof. See, Medical Applications of Controlled Release, Langer and Wise (eds.), 1974, CRC Pres., Boca Raton, Fla.; Controlled Drug Bioavailability, Drug Product Design and Performance, Smolen and Ball (eds.), 1984, Wiley, N.Y.; Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105. In yet another embodiment, a controlled release system can be placed in proximity of the therapeutic target, i.e., the brain, thus requiring only a fraction of the systemic dose (see, e.g., Goodson, in Medical Applications of Controlled Release, 1989, supra, vol. 2, pp. 115–138).

Other controlled release systems are discussed in the review by Langer (1990, *Science* 249:1527–1533).

The present invention also provides pharmaceutical compositions. Such compositions comprise a therapeutically effective amount of a Therapeutic, and a pharmaceutically acceptable carrier.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. The parental preparation can be enclosed in ampoules, disposable syringes or multiple dose vials made of glass or plastic.

These compositions can take the form of solutions, suspensions, emulsion, tablets, pills, capsules, powders, sustained-release formulations and the like. The composition can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the Therapeutic of the invention which will be effective in the treatment of a particular disorder or condition will depend on the nature of the disorder or condition, and can be determined by standard clinical techniques. In addition, in vitro assays such as those discussed in section 5.2 may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test bioassays or systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Modifications and variations of the compositions of the present invention, and methods for use, will be obvious to those skilled in the art from the foregoing detailed description. Such modifications and variations are intended to fall within the scope of the appended claims.

The following non-limiting examples demonstrate the discovery of troponin subunit inhibition of angiogenic stimulus induced endothelial cell proliferation, and means for determining the effective dosage of troponin subunit, fragment, or analog to inhibit angiogenesis, as well as for identifying troponin subunit fragments and analogs (i.e., those fragments or analogs of troponin subunit capable of inhibiting angiogenesis. The troponin subunit used in the examples is purified as described infra.

EXAMPLES

Example 1: Purification of Troponin subunit Components

Cardiac Troponin Isolation from Tissue

The procedures of Ebashi et al., 1968, *J. Biochem.* 64:465–477; Yasui et al., 1968, *J. Biol. Chem.* 243:735–742; Hartshorne et al., 1969, *Biochim. Biophys. Acta,* 175:30; Schaub et al., 1969, *Biochem. J.* 115:993–1004; Greaser et al., 1971, *J. Biol. Chem.* 246:4226–4233; and Greaser et al., 1973, *J. Biol. Chem.* 248:2125–2133 for purifying troponin can be used. Rabbit back and leg muscles are removed, cleaned of fat and connective tissue, and ground. The ground muscle (1 kg) is stirred for 5 min. in 2 liters of a solution containing 20 mM KCl, 1 mM $KHCO_3$, 0.1 mM $CaCl_2$, and 0.1 mM DTT.[1] The suspension is filtered through cheesecloth, and the washing of the residue is repeated four times. Two liters of 95% ethanol are then added to the washed residue and the solution filtered after 10 min. The ethanol extraction is repeated twice. The residue is then washed 3 times with 2 liters of diethyl ether for 10 min. Finally the residue is allowed to dry at room temperature for 2 to 3 hours.

The abbreviations used are: DDT, dithiothreitol; EGTA, ethylene glycol bis(β-aminoethyl ether)-N, N'-tetraacetate; SDS, sodium dodecyl sulfate; SE-, sulfoethyl.

The dried powder (from 1 kg of muscle) is extracted overnight at 22° with 2 liters of a solution containing 1M KCl, 25 mM Tris (pH 8.0), 0.1 mM $CaCl^2$, and 1 mM DTT. After filtration through cheesecloth, the residue is once more extracted with 1 liter of 1M KCl.

The extracts are combined and cooled to 4° C. Solid ammonium sulfate is added to produce approximately 40% saturation (230 g per liter). After 30 min. the solution is centrifuged and 125 g of ammonium sulfate is then added per liter of supernatant (60% saturation). After centrifugation the precipitate is dissolved in 500 ml of a solution containing 5 mM Tris (pH 7.5), 0.1 mM $CaCl_2$, and 0.1 mM DTT and dialyzed against 15 liters of the same solution for 6 hours and against a fresh solution overnight.

Solid KCl is added to a final concentration of 1M and 1M KCl solution is added to bring the volume to 1 liter. The pH is then adjusted to 4.6 by addition of HCl, and the tropomyosin precipitate is removed by centrifugation. The pH of the supernatant is adjusted to 7.0 with KOH, and 450 g of ammonium sulfate were added per liter (70% saturation). The precipitate is dissolved in a solution containing 5 mM Tris (pH 7.5, 0.1 mM $CaCl_2$, and 0.1 mM DTT, and dialyzed overnight against the same solution. Solid KCl is added to bring its concentration to 1M, the pH adjusted to 4.6, and the precipitate formed removed by centrifugation. The neutralized supernatant is dialyzed against 2 mM Tris (pH 7.5) until the Nessler reaction is negative. The final yield of troponin is usually 2.5 to 3.0 g per kg of fresh muscle.

Cardiac Troponin Isolation from Tissue

Bovine hearts are obtained approximately 30 min. after death and immediately cut open, rinsed of blood, and immersed in ice. The left ventricle is removed, trimmed of excess fat and connective tissue, and ground. All subsequent extraction and preparation steps are performed at 0°–3° except where noted. The ground muscle (500 g) is homogenized in a Waring Blender for 1 min. in 2.5 liters of solution containing 0.09M $KH_2PO_4$, 0.06M $K_2HPO_4$, 0.3M KCl, 5 mM 2-mercaptoethanol, pH 6.8. The homogenized muscle suspension is then stirred for 30 min. and centrifuged at 1000 ×g for 20 min. The precipitate is re-extracted for 30 min. and centrifuged. The residue is then washed with 2.5 liters of 5 mM 2-mercaptoethanol and centrifuged at 1000 ×g for 10 min., followed by two successive washings and centrifugations with 1.5 liters of 50 mM KCl, 5 mM Tris-HCl (pH 8.1/5), mM 2-mercaptoethanol. The residue is then washed and centrifuged twice with 1.5 liters of 50 mM Tris-HCl (pH 8.1), and 5 mM 2-mercaptoethanol. The volume of the residue is measured, and the residue is mixed with 0.5 volume of 3 M KCl, 50 mM Tris-HCl (pH 8.1), and 5 mM 2-mercaptoethanol. After a 16- to 20-hour extraction at 0°, the suspension is centrifuged at 15,000 ×g for 10 min. The sediment is discarded, and the supernatant is adjusted to pH 7.6 with 0.05 N HCl. The filamentous precipitate which forms upon pH adjustment is removed by filtering the extract through nylon gauze. The protein that precipitates between 30 and 50% ammonium sulfate saturation is collected, dissolved in a solution containing 1M KCl, and 1 mM potassium phosphate (pH 6.8), and 5 mM 2-mercaptoethanol, and dialyzed against the same solution for 4 hours and against a fresh solution overnight. The protein solution is clarified by centrifugation at 105,000 ×g for 30 min. The troponin is then purified by chromatography on a hydroxylapatite column with the protein being eluted between 0.08 and 0.10M phosphate. Greaser et al., 1972 *Cold Spring Harbor Symp. Quant. Biol.* 37:235–244. Rabbit cardiac troponin is prepared in a similar manner using a pooled batch of hearts which has been stored at −20° C. prior to extraction.

The troponin subunits are separated by DEAE-Sephadex chromatography in 6M urea. Bovine cardiac tropomyosin is prepared from the 50% ammonium sulfate saturation supernatant from the troponin extraction scheme (see above). Ammonium sulfate is added to 65% saturation, and the precipitate is dissolved in and dialyzed versus 1M KCl, 1 mM potassium phosphate (pH 7.0), and 5 mM 2-mercaptoethanol. The protein is then purified by hydroxylapatite chromatography.

Protein Determination—Protein concentrations are determined by the biuret method of Gornall et al. using bovine serum albumin as a standard. Gornall et al., 1949, *J. Biol. Chem.,* 177:751–766.

Separation of Components—A sequence of SP-Sephadex and DEAE-Sephadex chromatography gives complete separation of the three cardiac troponin components.

Recombinant Troponin Isolation and Reconstitution Protocols Troponin I and T

DNA encoding various troponin subunits and isoforms are known in the art. See, e.g., Wu et al., 1994, *DNA Cell. Biol.* 13:217–233; Schreier et al., 1990, *J. Biol. Chem.* 265:21247–21253; and Gahlmann et al., 1990, *J. Biol. Chem.* 265:12520–12528.

To express a troponin subunit, DNA encoding the subunit is subcloned into a high copy number expression plasmid, such as KP3998, using recombinant techniques known in the art.

To express the cloned cDNA, *E. coli* transformed with the insert-containing pKP1500 vector is grown overnight at 37° C., then inoculated into 4 liters of Luria-Bertani broth (LB) medium and grown at 42° C. until mid-log phase. Isopropyl-1-thio-β-D-galactopyranoside is then added to 0.5 mM, and the culture is allowed to grow at 42° C. overnight. Purification of expressed troponin subunit, fragment, or analog may be adapted from published procedures (Reinach et al., 1988, *J. Biol. Chem.* 250:4628–4633 and Xu et al., 1988, *J.*

Biol. Chem. 263:13962–13969). The cells are harvested by centrifugation and suspended in 20 ml of 20 mM Tris, 20% sucrose, 1 mM EDTA, 0.2 mM phenylmethylsulfonyl fluoride, 1 mg/ml lysozyme, pH 7.5. After incubation on ice for 30 min., 80 ml of 20 mM Tris, 1 mM EDTA, 0.2 mM phenylmethylsulfonyl fluoride, 0.5 mM DTT is added and the cells broken in a French press (SLM Instruments). The cell debris is pelleted; the supernatant is made 35% in saturated $(NH_4)_2SO_4$ and stirred on ice for 30 min. After sedimentation, the supernatant is made 50 mM in NaCl, 5 mM in $CaCl_2$, 1 mM in $MgCl_2$, and 1 mM in DTT and then loaded onto a 1.5 ×25-cm phenyl-Sepharose (Pharmacia LKB Biotechnology Inc.) column. The column is washed first with 50 mM Tris, 50 mM NaCl, 5 mM $CaCl_2$, 1 mM $MgCl_2$, 1 mM DTT, pH 7.5, then with 50 mM Tris, 1 mM NaCl, 0.1 mM $CaCl_2$, 1 mM DTT, pH 7.5, until no more protein is eluted. The crude troponin subunit is then eluted with 50 mM Tris, 1 mM EDTA, 1 mM DTT, pH 7.5. Fractions that contained troponin subunit, fragment, or analog are pooled, dialyzed against 25 mM Tris, 6M urea (United States Biochemical Corp.), 1 mM $MgCl_2$, 1 mM DTT, pH 8.0, and loaded onto a 1.5×25-cm DE52 (Whatman) column. The column is eluted with a 0–0.6M NaCl linear gradient. Troponin subunit, fragment, or analog eluted from the column is dialyzed against 0.1 mM $NH_4HCO_3$, 1 mM β-mercaptoethanol, lyophilized, and stored. Purity is assessed by SDS-polyacrylamide gel electrophoresis and UV spectrophotometry. Typical yields of 6 mg of purified recombinant troponin subunit, fragment, or analog/liter of bacterial culture are expected.

The lyophilized recombinant protein is resuspended in a take up buffer consisting of 6M urea, 20 mM Hepes (pH 7.5), 0.5M NaCl, 2 mM EDTA, and 5 mM DTT. The mixture is nutated at room temperature for 1 hour. The solution is then dialyzed at 4° C. for six hours with 1 exchange against a dialysis buffer consisting of 0.5M NaCl, 20 mM Hepes (pH 7.5), and 0.5 mM DTT.

Protein concentration is determined for each subunit at 280λ. The extension coefficient of Troponin I is 0.40 and Troponin T is 0.50.

Troponin C

The lyophilized recombinant protein is resuspended in a take up buffer consisting of 0.1M NaCl, 20 mM Hepes (pH 7.5), 2 mM EDTA, and 5 mM DTT. This solution is dialyzed for 6 hours at 4° C. with one exchange against a dialysis buffer of 0.1M NaCl, 20 mM Hepes (pH 7.5), and 0.5 mM DTT.

Protein concentration is determined by measuring absorbance at 280λ. The extension coefficient for troponin C is 0.18.

Reconstitution of Combined Subunits:

Protein concentrations having the same reconstitution molar ratios of troponin subunits C, I, and T are maintained for all various combinations. These concentrations of the respective proteins are combined in a reconstitution buffer consisting of 0.1M NaCl, 0.1M CaCl2, mM DTT, 5 mM Hepes (pH 7.5). Dialysis is for 20–24 hours at 4° C. with three exchanges over a dialysis buffer consisting of 0.1M NaCl, 0.1 m $CaCl_2$, 0.5 mM DTT, and 5 mM Hepes (pH 7.5).

Protein concentration is approximated by measuring absorption at 278λ. The troponin trimer has an extension coefficient of 0.45 at 278λ.

Example 2: Inhibition of Endothelial Cell Proliferation measured by DNA synthesis.

The inhibitory effect of troponin subunit, fragment, or analog on the proliferation of bFGF-stimulated EC can be measured according to the following procedure.

Endothelial cell DNA Synthesis:

On day one, 5,000 Bovine capillary endothelial cells in DMEM/10% CS/1% GPS are plated onto each well of a 96-well pregelatinized tissue culture plate. On day two, the cell media is changed to DMEM, 2% CS, 1% GPS, 0.5% BSA (complete medium), supplemented with 10 µl of 1 mg/ml "cold" thymidine per 50 ml of medium. On day three, test samples in complete medium are added in duplicate. Additionally, bFGF is added in each well except for the appropriate controls, to a final concentration of 0.2 ng/well. On day four, 5 µl of 1:13 diluted $^3$H-Thymidine stock is added to each well and the plate is incubated for 5–6 hours. Following incubation, the medium is aspirated, and the remainder is rinsed once with PBS, then twice for 5 minutes each with methanol followed by two rinses each for 10 minutes with 5% TCA. The cells well contents are then rinsed with water three times, dried to the plate, and 100 µl of 0.3 N NaOH is added to each well. The contents of the well are then transfered to the scintillation counter vials and 3 mls of Ecolume added to each vial. Samples are then counted on the scintillation counter.

3T3 Cell DNA Synthesis:

DNA synthesis in bFGF-stimulated 3T3 cells provides a control with which to evaluate results obtained for bFGF stimulated endothelial cell proliferation. DNA synthesis in the 3T3 cells can be determined according to the following method.

BALB/c 3T3 cells are trypsinized and resuspended at a concentration of $5 \times 10^4$ cells/ml. Aliquots of 200 µl are plated into 0.3 $cm^2$ microtiter wells (Microtest II tissue Culture Plates, Falcon). After reaching confluence, in a period of 2 to 3 days, the cells are further incubated for a minimum of 5 days in order to deplete the media of growth promoting factors. These growth conditions yield confluent monolayers of non-dividing BALB/c 3T3 cells. Test samples are dissolved in 50 µl of 0.15M NaCl and added to microtiter wells, along with [$^3$H]TdR. After an incubation of at least 24 hours, the media is removed and the cells are washed in PBS. Fixation of the cells and removal of unincorporated [$^3$H]TdR is accomplished by the following successive steps; addition of methanol twice for periods of 5 minutes, 4 washes with $H_2O$, addition of cold 5% TCA twice for periods of 10 minutes, and 4 washes with $H_2O$. DNA synthesis is measured either by liquid scintillation counting or by autoradiography using a modification of the method described by Haudenschild et al., 1976, M. Exp. Cell Res. 98:175. For scintillation counting, cells are lysed in 150 µl of 0.3 N NaOH and counted in 5 ml. of Insta-Gel liquid scintillation cocktail (Packard) using a Packard Tri-Carb liquid scintillation counter. Alternatively, autoradiography may be used to quantitate DNA synthesis by punching out the bottoms of the microtiter wells and mounting them on glass slides with silastic glue. The slides are dipped in a 1 g/ml solution of NTB2 nuclear track emulsion (Kodak) and exposed for 3–4 days. The emulsion is developed with Microdol-X solution (Kodak) for 10 minutes, rinsed with distilled $H_2O$, and fixed with Rapid Fixer (Kodak) for three minutes. The autoradiographs are stained with a modified Giemsa stain. At least 1000 nuclei are counted in each well and DNA synthesis, expressed as the percentage of nuclei labeled. Cell division is measured by counting the number of cells in microtiter wells with the aid of a grid after 40–48 hour incubations with test samples.

Example 3: Inhibition of Endothelial Cell Proliferation measured by calorimetric determination of cellular acid phosphatase activity and electronic cell counting A quick and sensitive screen for inhibition of EC proliferation in response to treatment with a troponin subunit, analog, or derivative of the invention involves incubating the cells in the presence of varying concentrations of the inhibitor and determining the number of endothelial cells in culture based on the calorimetric determination of cellular acid phosphatase activity, described by Connolly, et al., 1986, *J. Anal. Biochem.* 152:136–140.

We measured the effect of troponin on the proliferation of capillary endothelial cells (EC) in an assay which measures the ability of this protein to interfere with stimulation of endothelial cell proliferation by a known angiogenesis factor (bFGF).

Capillary endothelial cells and Balb/c 3T3 cells were separately plated (2 ×10$^3$/0.2 ml) onto gelatin-coated 96-well tissue culture dishes on day 1. On day 2, cells were refed with Dulbecco's modified Eagle's medium (Gibco) with 5% calf serum (Hyclone) (DMEM/5) and bFGF (10 ng/ml) (FGF Co.) and increasing concentrations of the troponin subunit. These substances were added simultaneously in volumes that did not exceed 10% of the final volume. Wells containing phosphate buffered saline (PBS) (Gibco) alone and PBS+bFGF were included as controls. On day 5, media was removed and cells were washed with PBS and lysed in 100 $\mu$l of buffer containing 0.1M sodium acetate (pH 5.5), 0.1% Triton X-100™ and 100 mM p-nitrophenyl phosphate (Sigma 104 phosphatase substrate). After incubation for 2 hours at 37° C., the reaction was stopped with the addition of 10 $\mu$l of 1 N NAOH. Color development was determined at 405 nm using a rapid microplate reader (Bio-Tek).

Percent inhibition was determined by comparing the cell number of wells exposed to stimulus with those exposed to stimulus and troponin subunits.

All three troponin subunits were found to inhibit bFGF-stimulated EC proliferation, as measured by the calorimetric assay.

Troponin C inhibited bFGF-stimulated endothelial cell proliferation in a dose-dependent manner in all concentrations tested (FIG. 1). Percent inhibition of bovine endothelial cell proliferation ("BCE") was 54%, 86%, 83%, and 100% at concentrations of 280 nM, 1.4 $\mu$M, 2.8 $\mu$M and 5.6 $\mu$M, respectively. An inhibition of 100% was observed at a concentration of 20 ug/well (5.6 $\mu$M). IC$_{50}$ represents the concentration at which 50% inhibition of bFGF growth factor-induced stimulation was observed. The IC$_{50}$ of troponin C was determined to be 278 nM.

Figure 2:
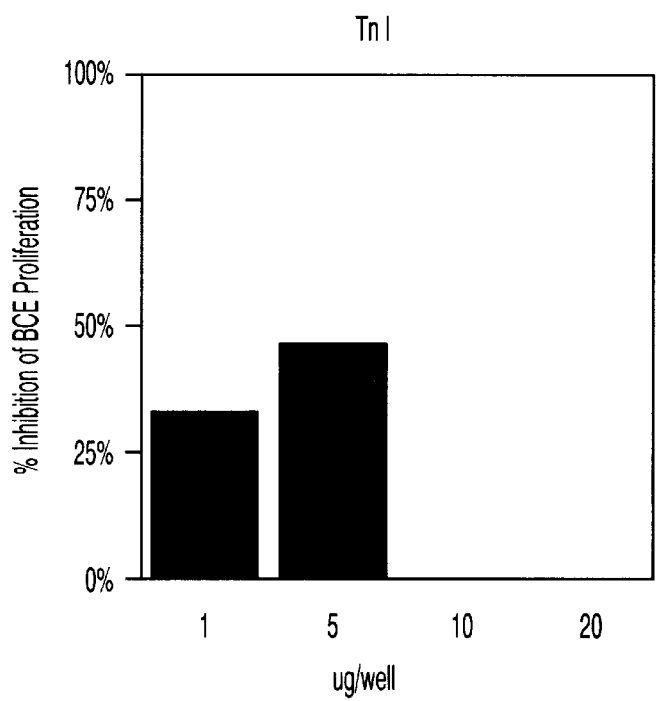
FIG. 2. Inhibition of capillary BCE proliferation by troponin I. Percent inhibition of bFGF-stimulated BCE proliferation is shown as a function of troponin I concentration (nM). Percent inhibition was determined as described in FIG. 1. Well volume was 200 μl.

Troponin I inhibited bFGF-stimulated BCE proliferation at concentrations of 1 and 5 ug/well, but inhibition was not observed in the sample tested at 10 ug/well (FIG. 2). The percent inhibition of BCE was 33% and 46% at concentrations of 240 nM and 1.2 $\mu$M, respectively. The IC$_{50}$ of troponin I was determined to be 1.14 $\mu$M.

Figure 3:
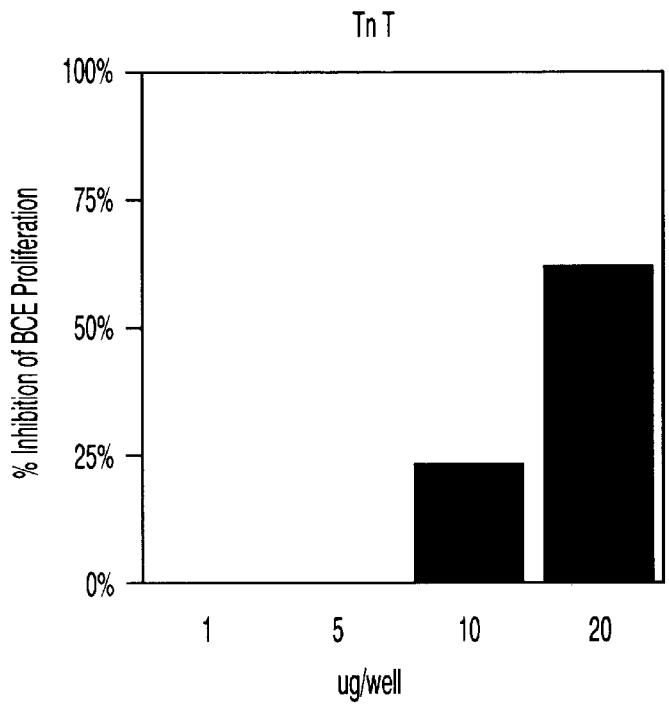
FIG. 3. Inhibition of capillary BCE proliferation by troponin T. Percent inhibition of bFGF-stimulated BCE proliferation is shown as a function of troponin T concentration (nM). Percent inhibition was determined as described in FIG. 1. Well volume was 200 μl.

Troponin T inhibited bFGF-stimulated EC proliferation at concentrations of 10 and 20 ug/well, but not at concentrations of 1 and 5 $\mu$g/well (FIG. 3). BCE proliferation was inhibited 23% and 62% at 1.6 $\mu$M and 3.3 $\mu$M, respectively. The IC$_{50}$. of troponin T was determined to be 2.14 $\mu$M.

Figure 4:
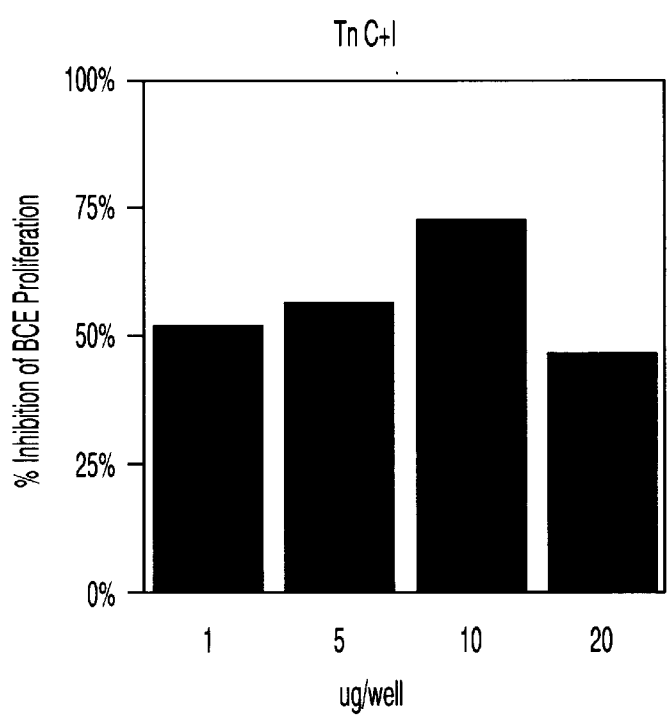
FIG. 4. Inhibition of BCE proliferation by troponins C and I. Percent inhibition of bFGF-stimulated BCE proliferation is shown as a function of troponin I and C concentration (nM). Percent inhibition was determined as described in FIG. 1. Well volume was 200 μl.

The combination of troponin subunits C and I inhibited EC at all concentrations tested (FIG. 4). The percent inhibition of proliferation of BCE was 52%, 540% 73% and 47% at 130 nM, 645 nM, 1.3 $\mu$M and 2.6 $\mu$M, respectively. The IC$_{50}$ of this combination was determined to be 110 nM.

Figure 5:
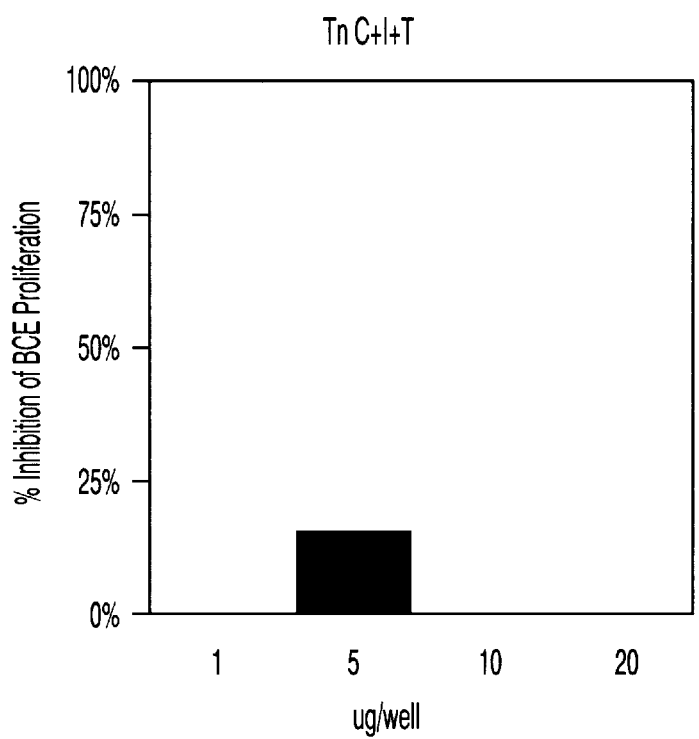
FIG. 5. Inhibition of capillary BCE proliferation by troponin C, I and T. Percent inhibition of bFGF-stimulated BCE proliferation is shown as a function of troponin C, I, and T concentration (nM). Percent inhibition was determined as described in FIG. 1. Well volume was 200 μl.

The combination of troponin subunits C, I and T was observed to inhibit bFGF-stimulated BCE proliferation by 16% at a concentration of 360 nM (5 ug/well, FIG. 5).

The troponin samples tested had no detectable inhibitory effect on the growth of Balb/c 3T3 cells, a non-endothelial cell type.

Example 4: Inhibition of Capillary Endothelial Cell Migration by trotonin

Determination of the ability of the troponin subunit, derivative, or analog to inhibit the angiogenic process of capillary EC migration in response to an angiogenic stimulus, can be determined using a modification of the Boyden chamber technique is used to study the effect of troponin subunit, derivative, or analog on capillary EC migration. Falk et al., 1980, *J. Immunol.* 118:239–247 (1980). A blind-well Boyden chamber, consists of two wells (upper and lower) separated by a porous membrane. *J. Exp. Med.* 115:453–456 (1962). A known concentration of growth factor is placed in the lower wells and a predetermined number of cells and troponin subunit, derivative, or analog is placed in the upper wells. Cells attach to the upper surface of the membrane, migrate through and attach to the lower membrane surface. The membrane can then be fixed and stained for counting, using the method of Glaser et al., 1980, *Nature* 288:483–484.

Migration is measured using blind well chambers (Neuroprobe, no. 025–187) and polycarbonate membranes with 8 micron pores (Nucleopore) precoated with fibronectin (6.67 $\mu$g/ml in PBS) (human, Cooper). Basic FGF (Takeda Co.) diluted in DMEM with 1% calf serum (DMEM/1) is added to the lower well at a concentration of 10 ng/ml. The upper wells receive 5×10$^5$ capillary EC/ml and increasing concentrations of purified troponin subunit, derivative or analog is used within 24 hours of purification. Control wells receive DMEM/1, either with or without bFGF. The migration chambers are incubated at 37° C. in 10% CO2 for 4 hours. The cells on the upper surface of the membrane are then wiped off by drawing the membrane over a wiper blade (Neuroprobe). The cells which have migrated through the membrane onto the lower surface are fixed in 2% glutaraldehyde followed by methanol (4° C.) and stained with hematoxylin. Migration is quantified by counting the number of cells on the lower surface in 16 oil immersion fields and comparing this number with that obtained for the control.

Example 5: Inhibition in vivo of Neovascularization by troponin as determined by the chick chorioallantoic membrane assay The chick chorioallantoic membrane assay (CAM), may be used to determine whether troponin subunit, derivative or analog is capable of inhibiting neovascularization in vivo. Taylor and Folkman, 1982, *Nature (London)* 297:307–312. The effect of troponin subunit, derivative or analog on growing embryonic vessels is studied using chick embryos in which capillaries appear in the yolk sac at 48 h and grow rapidly over the next 6–8 days.

Three day post fertilization chick embryos are removed from their shells and placed in plastic petri dishes (1005, Falcon). The specimens are maintained in humidified 5% $CO_2$ at 37° C. On day 6 of development, samples of purified troponin subunit, derivative or analog are mixed in methylcellulose disks and applied to the surfaces of the growing CAMs above the dense subectodermal plexus. Control specimens in which CAMs are implanted with empty methylcellulose disks are also prepared. The CAMs are injected intravascularly with India ink/Liposyn to more clearly delineate CAM vascularity. Taylor et al., 1982, *Nature* 297:307–312.

Following a 48 hour exposure of the CAMs to the troponin subunit, derivative, or analog, the area around the implant is observed and evaluated. Test specimens having avascular zones completely free of India-ink filled capillaries surrounding the test implant indicate the presence of an inhibitor of embryonic neovascularization. In contrast, the control specimens show neovascularization in close proximity or in contact with the methylcellulose disks.

Histological mesodermal studies are preformed on the CAMs of test and control specimens. The specimens are embedded in JB-4 plastic (Polysciences) at 4° C. and 3 μm sections are cut using a Reichert 2050 microtome. Sections are stained with toluidine blue and micrographs are taken on a Zeiss photomicroscope using Kodak TM x100 and a green filter.

Example 6: Inhibition in vivo of Neovascularization by troponin as determined by the rabbit corneal Pocket assay Male NZW rabbits weighing 4–5 lbs. are anesthetized with intravenous pentobarbital (25 mg/kg) and 2% xylocaine solution is applied to the cornea. The eye is proptosed and rinsed intermittently with Ringer's solution to prevent drying. The adult rabbit cornea has a diameter of approximately 12 mm. An intracorneal pocket is made by an incision approximately 0.15 mm deep and 1.5 mm long in the center of the cornea with a No. 11 scalpel blade, using aseptic technique. A 5 mm-long pocket is formed within the corneal stroma by inserting a 1.5 mm wide, malleable iris spatula. In the majority of animals, the end of the corneal pocket is extended to within 1 mm of the corneal-scleral junction. In a smaller series of 22 rabbits implanted with tumor alone, pockets are placed at greater distances—2–6 mm from the corneal-scleral junction by starting the incision away from the center.

In the first assay, polymer pellets of ethylene vinyl acetate (EVAc) copolymer are impregnated with test substance and surgically implanted in a pocket in the rabbit cornea approximately 1 mm from the limbus. When this assay system is being used to test for angiogenesis inhibitors, either a piece of V2 carcinoma or some other angiogenic stimulant is implanted distal to the polymer, 2 mm from the limbus. On the opposite eye of each rabbit, control polymer pellets that are empty are implanted next to an angiogenic stimulant in the same way. In these control corneas, capillary blood vessels start growing towards the tumor implant in 5–6 days, eventually sweeping over the blank polymer. In test corneas, the directional growth of new capillaries from the limbal blood vessels towards the tumor occurs at a reduced rate and is often inhibited such that an avascular region around the polymer is observed (FIG. 1). This assay is quantitated by measurement of the maximum vessel lengths with a stereoscopic microscope.

We claim:

1. A method of inhibiting atopic angiogenesis in a subject, having a disease or disorder causing atopic angiogenesis comprising applying to a site of atopic angiogenesis an amount of a peptide that is effective to inhibit angiogenesis, in which the peptide is:
   a. an inhibitor of bFGF-stimulated bovine endothelial cell proliferation having an $IC_{50}$ of at least 10 μM;
   b. greater than 75 amino acids in length; and
   c. greater than 80% homologous with a subunit selected from the group consisting of human fast-twitch troponin I subunit (SEQ. ID. NO:2), human fast-twitch troponin C subunit (SEQ. ID. NO:1) and human fast-twitch troponin T subunit (SEQ. ID. NO:3).

2. The method of claim 1, in which the subunit is human fast-twitch troponin C (SEQ. ID. NO:1) or human fast-twitch troponin I.

3. The method of claim 2, in which the disease disorder is a solid tumor.

4. The method of claim 2, in which the tumor is a tumor of the central nervous system.

5. The method according to claim 2, in which the disease or disorder is an ophthalmologic disease or disorder.

* * * * *